United States Patent [19]

Bak et al.

[11] Patent Number: Plant 7,735

[45] Date of Patent: Dec. 3, 1991

[54] GUZMANIA PLANT NAMED MORADO

[75] Inventors: Gerardus J. Bak, Assendelft; Nicolaas D. Steur, Oude Niedorp; Elly Bak, Assendelft, all of Netherlands

[73] Assignee: Corn. Bak B.V., Netherlands

[21] Appl. No.: 526,997

[22] Filed: May 22, 1990

[51] Int. Cl.[5] ..... A01H 5/00

[52] U.S. Cl. ..... Plt./88

[58] Field of Search ..... Plt./88, 88.1, 88.8

*Primary Examiner*—Howard J. Locker

*Attorney, Agent, or Firm*—Foley & Lardner

[57] ABSTRACT

A new cultivar of Guzmania named Morado, characterized by its large bipinnate and lilac color inflorescence, superior floral bract production, strong compact growth habit, and its numerous and long floral branches.

2 Drawing Sheets

The present invention relates to a new and distinct cultivar of Guzmania, a genus within the family bromeliaceae, hereinafter referred to by the cultivar name Morado. The new cultivar is a hybrid resulting from a cross of unnamed parent plants identified below.

Guzmania comprise a genus of over 100 species of evergreen perennials suitable for cultivation in the home or under glass. Guzmania are predominantly epiphytic with a few terrestrial species and are native to the tropics. For the most part the species vary in diameter from 7 or 8 inches to 3 or 4 feet and have rosettes of glossy, smooth edged leaves.

Floral bracts of Guzmania frequently have brilliant colors and may last for many months. The range of flower colors for Guzmania is generally from yellow through orange but may also include flame red and red-purple. White or yellow, tubular, three petalled flowers may also appear on a stem or within the leaf rosette but are usually short lived.

Guzmania may be advantageously grown as pot plants for greenhouse or home use. Desirably the plants are shaded from direct sunlight and during the spring to autumn period, the central vase-like part of the leaf rosette is normally filled with water.

Guzmania is native to tropical America. Leaves of the Guzmania are usually formed as basal rosettes which are stiff and entire and in several vertical ranks. Guzmania have terminal spikes or panicles which are often bracted with petals united in a tube about as long as the calyx.

Asexual propagation of Guzmania is frequently done through the use of tissue culture practices. Propagation can also be from off-shoots produced by the plant which may then be rooted. The resulting plantlets are detached from the mother plant and may be potted up in a suitable growing mixture.

The new cultivar Morado is a product of a planned breeding program and was originated by the inventors from a cross made during such a program in Assendelft, The Netherlands, in 1985. The male, or pollen parent, was an unnamed selection from *Guzmania albo-rosea* identified by the breeding number 85-332-01. The female, or seed parent, was an unnamed selection from *Guzmania blassii* identified by the breeding number 85-332-02. Both parents have a degree of homozygosity such that the progeny of the cross were and continue to be surprisingly uniform. The selection comprising the new variety was chosen after commencement of flowering of the progeny in 1988, and subsequent asexual propagation by offshoots has demonstrated that the combination of characteristics as herein disclosed for the new cultivar Morado are firmly fixed and are retained through successive generations of asexual reproduction.

Morado is particularly characterized by the following:

1. Strong, compact growth habit.
2. A lilac-creme inflorescence.
3. Superior floral bract production.
4. Large bipinnate inflorescence.
5. Its long floral branches.
6. Its long lasting habit.
7. Its vertical scape containing approximately 14 branches, each of which has a bract on its underside. The number of flowers per branch is approximately 12.
8. Its leaves which extend outwardly from the base away from the scape to form a full plant with relatively long cascading leaves.

Perhaps the closest comparison cultivar is Marlebeca. Several of the above noted distinguishing characteristics of Morado also serve to distinguish Morado from Marlebeca, particularly the length of the extended floral branches of Morado, and the red-purple (lilac) floral bracts, as opposed to the red floral bracts of Marlebeca.

Morado has not been tested under all available environmental conditions and the phenotype may vary with variations in environmental conditions such as temperature, light intensity, day length and humidity.

The accompanying color photographic drawings show typical characteristics of Morado, with colors being as true as possible with illustrations of this type.

Sheet 1 comprises a perspective view of a full plant with floral bracts.

Sheet 2 contains a more enlarged showing of the floral bracts and inflorescence.

In the following description, color references are made to the Royal Horticultural Society Colour Chart (R.H.S.).

The following traits have been repeatedly observed and in combination distinguish Morado as a new and distinct cultivar. These observations, measurements and descriptions have been performed under greenhouse conditions in Assendelft, The Netherlands.

I. Plant:

*Form.*—Funnel form rosette.

*Height.*—Approximately 70 cm high when flowering; approximately 40 cm without flowers and bracts.

*Growth habit.*—Stemless.

*Diameter.*—Average approximately 100 cm.

II. Foliage:

*Size of leaf.*—Approximately 20–60 cm long; leaves extend away from the base to form a full plant.

*Shape of leaf.*—Lanceolate.

*Surface texture.*—Smooth.

*Variegation.*—None.

*Color.*—Upperside; RHS 144A. Underside; RHS 146B. At the base: anthocyanous coloring, 59A.

*Average number of leaves.*—17.

III Bracts:

*Length.*—Primary bracts approximately 4.5–7.5 cm, with the lower bracts being longer than the upper bracts.

*Width.*—At the base, primary bracts are approximately 4 cm.

*General shape.*—Lanceolate.

*Number.*—Approximately 14 primary bracts.

*Texture.*—Smooth.

*Margin.*—Entire.

*Color.*—58A/64B.

IV. Flowers:

*Borne.*—On branches; number of branches on scape is approximately 14, with about 12 flowers per branch; very floriferous.

*Shape of inflorescence.*—Bipinnate.

*Individual flowers.*—(1) Length: Total length of flower is about 3.5 cm; length of flower bracts is about 1.5 cm, and length of sepals is about 2.5 cm, and sepals adopt color of corolla. (2) Quantity: Approximately 12 flowers per branch, and approximately 14 branches, depending on the size of plant and inflorescence. (3) Color of bracts: 58A–64B. (4) Corolla: Approximately 3.5 cm in length; color RHS 5C.

*Time of blooming.*—In a fully grown plant, flowers start approximately 15 weeks after induction, and at any time of the year.

*Duration of blooms.*—Each flower blooms 1 day and the total duration of blooming is about 6 weeks.

V. Reproductive organs: Stamens, pistil and receptacle are hidden within the corolla.

VI. Seed characteristics: Sterile hybrid, therefore no seed.

We claim:

1. A plant of a new and distinct cultivar of Guzmania plant named Morado, as illustrated and described.

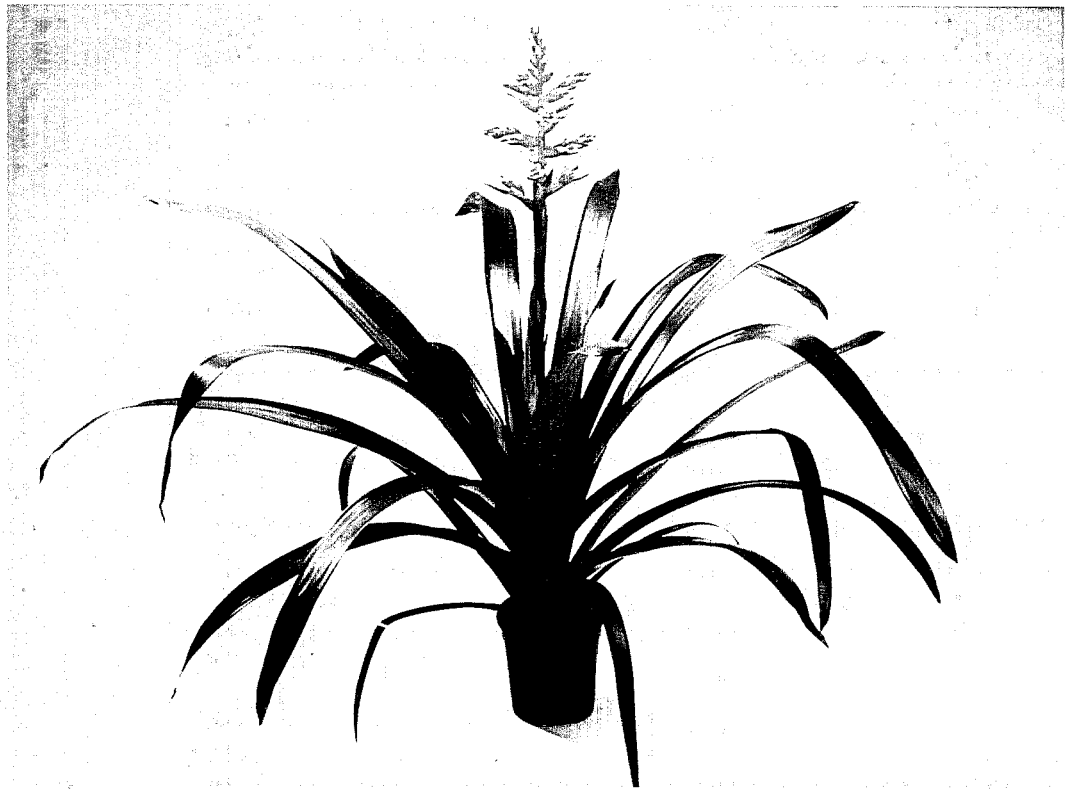

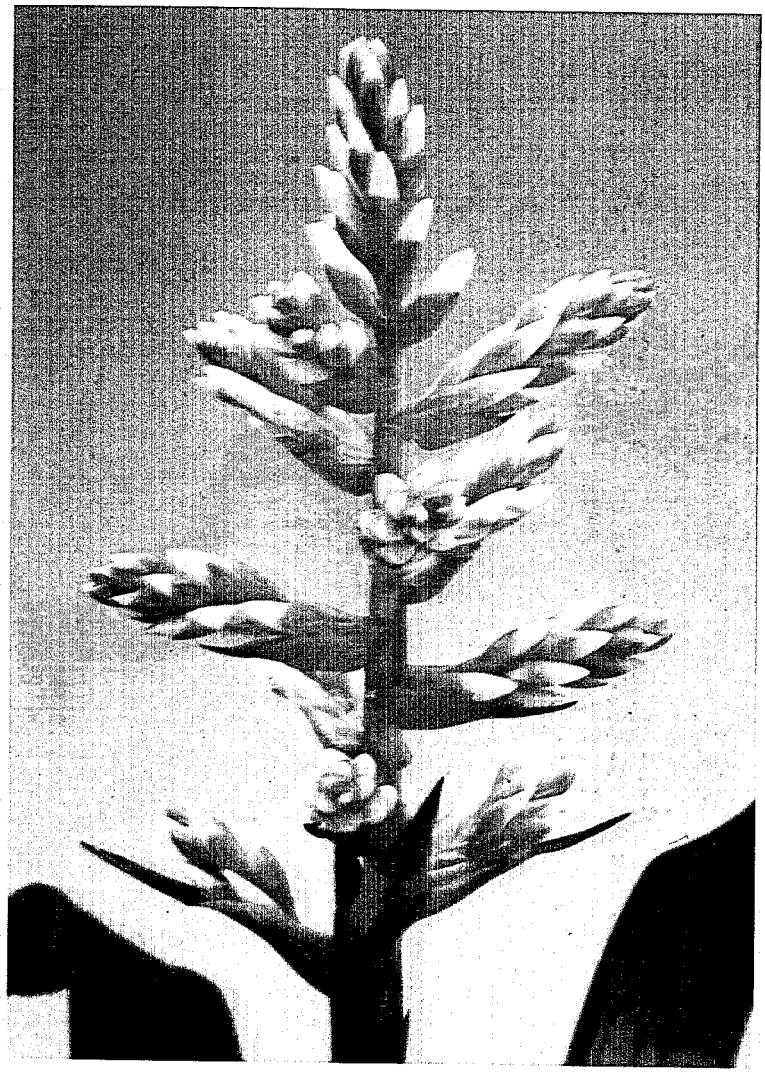

* * * * *